United States Patent [19]

Strobl et al.

[11] Patent Number: 4,579,125
[45] Date of Patent: Apr. 1, 1986

[54] REAL-TIME EEG SPECTRAL ANALYZER

[75] Inventors: Frederick T. Strobl, Chaska; Daniel E. Cohen, Eden Prairie, both of Minn.

[73] Assignee: CNS, Inc., Eden Prairie, Minn.

[21] Appl. No.: 572,868

[22] Filed: Jan. 23, 1984

[51] Int. Cl.$^4$ .............................. A61B 5/04; A61B 5/05
[52] U.S. Cl. ...................................... 128/731; 128/733
[58] Field of Search ........................ 128/731, 732, 733

[56] References Cited

U.S. PATENT DOCUMENTS

| | | | |
|---|---|---|---|
| 4,244,376 | 1/1981 | Fisher et al. ......................... | 128/731 |
| 4,328,491 | 5/1982 | Demetrescu et al. ........... | 128/731 X |
| 4,417,591 | 11/1983 | Culver ................................. | 128/731 |
| 4,493,327 | 1/1985 | Bergelson et al. .................. | 128/731 |

*Primary Examiner*—Donald R. Valentine
*Attorney, Agent, or Firm*—Kinney & Lange

[57] ABSTRACT

An electroencephelograph (EEG) signal analysis system automatically determines and displays, on a real-time basis, the frequency content of spontaneous EEG signals from the brain. The analog EEG signals from a plurality of channels are sampled and converted to digitized EEG waveforms during a continuing sequence of epochs of predetermined time duration. The digitized EEG waveform for each epoch and channel is transformed from the time domain to the frequency domain to produce a frequency spectrum representing amplitude of the EEG signal as a function of frequency. The digital data is screened both prior and subsequent to the transformation to identify those epochs which contain artifacts. During each update period, the frequency spectra for each channel from the artifact-free epochs are averaged. The amplitudes of each averaged frequency spectrum for frequencies in each of four basic frequency bands are then summed. The result is an amplitude value for each of the four frequency bands at each channel. The four amplitude values are used to update a display which contains a graphical representation of the amplitude in each of the four bands in a different color. The amplitude values are also compared with previously recorded base line values, and an audible or visual warning indication is provided when predetermined variances from the base line values occur.

43 Claims, 8 Drawing Figures

REAL-TIME EEG SPECTRAL ANALYZER

BACKGROUND OF THE INVENTION

1. Field of the Invention

The present invention relates to an electroencephalograph (EEG) signal analysis system which determines and displays, on a real-time basis, the frequency content of EEG signals from the brain.

2. Description of the Prior Art

An electroencephalograh (EEG) is a device which measures and records brain wave activity by sensing electrical potential of a patient's scalp, cortex or cerebrum at various sites. Each EEG channel corresponds to a particular electrode combination attached to the patient. The sensed EEG potential at each channel is amplified by a differential amplifier, and the amplifier output signal is typically used to control movement of a recording pen of a polygraph. The EEG record is a long strip of polygraph paper containing a waveform for each EEG channel. The polygraph paper is driven at a predetermined rate (e.g. 30 millimeters per second) and is graduated to represent predetermined time increments. A neurologist must evaluate the EEG record to determine abnormalities in the EEG waveforms.

EEG signals exhibit different frequencies depending upon brain activity. The EEG signal frequencies are classified into four basic frequency bands, which are generally referred to as "delta" (0 to 3.5 Hertz); "theta" (4 to less than 8 Hertz); "alpha" (8 to 13 Hertz); and "beta" (greater than 13 Hertz). The neurologist determines the predominant frequency of a particular channel during a particular time period by measuring the period of the EEG signal waveform shown on the EEG record. This requires considerable training and is highly dependent upon the skill of the neurologist, since the EEG signal waveform typically includes multiple frequency components.

In general, electronic equipment developed in the past for EEG analysis has been designed primarily for the acquisition of data, with little emphasis on the analysis of that data. Although computers were introduced into EEG technology in the early 1970's, there has been limited acceptance of computer-assisted EEG analysis due to a limited number of channels which are analyzed and a lack of an intuitive display. Existing computerized EEG technology has required a high degree of specialized knowledge to understand the information being displayed and, as a result, the market for that technology has been limited to a relatively small number of specialists in the field of electroencephalography.

One type of EEG signal analysis which has been performed by computers in the past has been called a "spectral analysis" or "compressed spectral array". In this type of analysis, the analog EEG signal for each channel is periodically sampled, converted to a digital value and stored. The stored digital data represents an EEG signal waveform (i.e. the amplitude of the EEG signal as a function of time). The computer converts the stored digital data from the time domain to the frequency domain by means of a Fast Fourier Transform (FFT) algorithm. The transformed data represents a frequency spectrum (i.e. amplitude or power of the EEG signal as a function of frequency). The computer provides a printout or display which is formed by a series of staggered two-axis graphs of amplitude versus frequency representing the frequency spectra from different time periods or epochs. The resulting display looks somewhat similar to a mountain range.

Compressed spectral array analysis has a number of significant disadvantages. First, it uses an extremely complex and nonintuitive form of display, which requires a great deal of skill to interpret. Second, the display can only be interpreted at a very close range, even by skilled personnel. Third, compressed spectral array analysis is not performed on a real-time basis in more than four channels.

There are a number of important applications of EEG analysis which have not been possible or have been extremely inconvenient with the prior art EEG systems. One important application is in the monitoring of cerebral functions within an operating room during a surgical procedure such as a carotid endarterectomy.

About forty percent of the blood flow to the human brain is provided by each of the two carotid arteries. These arteries can become hardened, thus limiting blood flow to the brain, and in that case a carotid endarterectomy is necessary to strip the carotid arteries.

One of the critical decisions during a carotid endarterectomy is whether the patient will need a shunt during the time when the artery is clamped and is being stripped. Some patients have sufficient blood flow to the brain from other areas so that the clamping of the carotid artery does not endanger the patient's brain due to insufficient blood flow. In a substantial number of cases, however, the blood flow is insufficient, and the clamping of the artery can cause the patient to have a stroke unless a shunt is provided. Unfortunately, it is almost never possible to know beforehand whether a shunt will be necessary. The problem with using a shunt is that it increases the chance of the patient having a stroke by about ten percent, because blood clots tend to adhere to the shunt, clots break off from the unit, or the inside of the vessel may tear and block the artery.

The most sensitive technique for determining whether a shunt will be needed during a carotid endarterectomy involves monitoring cerebral activity by means of EEG equipment. EEG monitoring has not, however, found wide use because it is very tedious and requires the presence of a trained neurologist to interpret the EEG record which is produced. Having a neurologist as well as EEG technicians in the operating room for long periods of time simply for the purpose of EEG monitoring significantly increases the total cost of the surgery. There is a need for an EEG signal analyzer which will automatically analyze EEG signals on a real-time basis during surgery, and which will provide an intuitive output which can be easily understood by the surgeon without the need for the presence of a neurologist during surgery and which provides an audible warning.

Other areas in which improvements in EEG technology would be desirable include the monitoring of patients or subjects during altered states of awareness or during psychological experimentation or assessment, monitoring in intensive care units and recovery rooms, and automatic interpretation of routine outpatient EEG. At the present time, monitoring using EEG typically involves the use of FM tape recorders which record the EEG signals for subsequent off-line analysis. This is a very costly procedure, in that the cost of the recording equipment increases significantly with each additional channel to be recorded. There is no on-line (or real-time) dynamic monitoring possible, since the EEG signals are being recorded for subsequent analysis.

The lack of on-line or real-time updates in the prior art significantly limits the types of monitoring which can be performed and the utility of those types of monitoring which are possible.

SUMMARY OF THE INVENTION

The present invention is an improved EEG signal analysis system and method which determines and displays, on a real-time basis, the frequency content of EEG signals from the brain. In the present invention, EEG signals from multiple channels are sampled, digitized and stored during a continuing sequence of epochs of predetermined time duration. For each epoch, a digitized waveform is stored for each channel.

The digitized waveforms for each epoch and channel are transformed from the time domain to the frequency domain. The result is a frequency spectrum for each domain and epoch.

For each channel, the frequency spectra from a number of epochs constituting an update period are averaged to produce an average frequency spectrum. The average frequency spectrum for each channel is then separated into predetermined frequency bands, and an amplitude value for each frequency band at that channel during the update period is derived based upon the sum of all of the amplitudes for frequencies within that band. The result, therefore, is an amplitude value for each channel in each of the selected frequency bands.

An output indicative of cerebral activity is then provided based upon the amplitude values for the selected frequency bands for each channel. The process is repeated on a continuing basis, and the output is updated on a periodic, real-time basis.

In preferred embodiments of the present invention, the data collected during each epoch is subjected to analysis which detects the presence of artifacts, and those epochs containing artifacts are not used in deriving the frequency band amplitude values upon which the output is based. The artifact rejection preferably includes analysis of the data both prior to and subsequent to the transformation from the time domain to the frequency domain.

Artifact rejection prior to the transformation preferably includes rejecting any epoch including a digitized waveform with an amplitude greater than a predetermined value (which indicates saturation of the analog-to-digital converter) and rejecting any epoch which exhibits high amplitudes at anterior channels (which indicate the presence of eye artifacts). Artifact rejection after the transformation to the frequency domain preferably includes rejecting any epoch which exhibits high frequency components from temporal channels (which indicates muscle artifacts). Also rejected is any epoch which exhibits unusually large amplitudes in the delta frequency band at two channels which share a common electrode, or which exhibits a large 60 Hertz component, since both of these conditions indicate the likelihood of loose leads to an EEG electrode.

Because of the speed with which the calculations are performed in the present invention, more time can be spent on artifact rejection, giving a more sophisticated analysis than is currently available.

In preferred embodiments of the present invention, the output provided by the present invention includes an easily understandable and intuitive display which can be used for monitoring EEG signals on a real-time basis during surgical procedures. One embodiment of the display is in the form of a plurality of circles or squares representing each of the EEG channels arranged over a graphic of a head. Each of the circles or squares is divided into four sectors representing the four frequency bands of interest (delta, theta, alpha and beta). Each sector is displayed in a different color, and the percentage size of each sector is determined by the ratio of the amplitude value for that frequency band to the sum of the amplitude values for all four bands. In addition, the area of the circle or square changes as a function of variance from a previously stored base line value for that channel.

Another embodiment uses a plurality of bar graphs over a head graphic. Each EEG channel has a bar graph representing each of the four frequency bands and a total of the four bands.

In another embodiment, the displays provide bar graphs for each channel which represent the frequency band amplitude values over a series of update periods. This graph provides an indication of trends in the frequency content of the EEG signals from the various channels.

In order to further assist a surgeon or other medical personnel, the present invention also preferably provides a warning signal (either audible, visual, or both) when a selected amplitude value or a combination of amplitude values at a particular channel varies by greater than a predetermined amount from a corresponding base line value.

DETAILED DESCRIPTION OF THE PREFERRED EMBODIMENTS

Figures 1, 2:
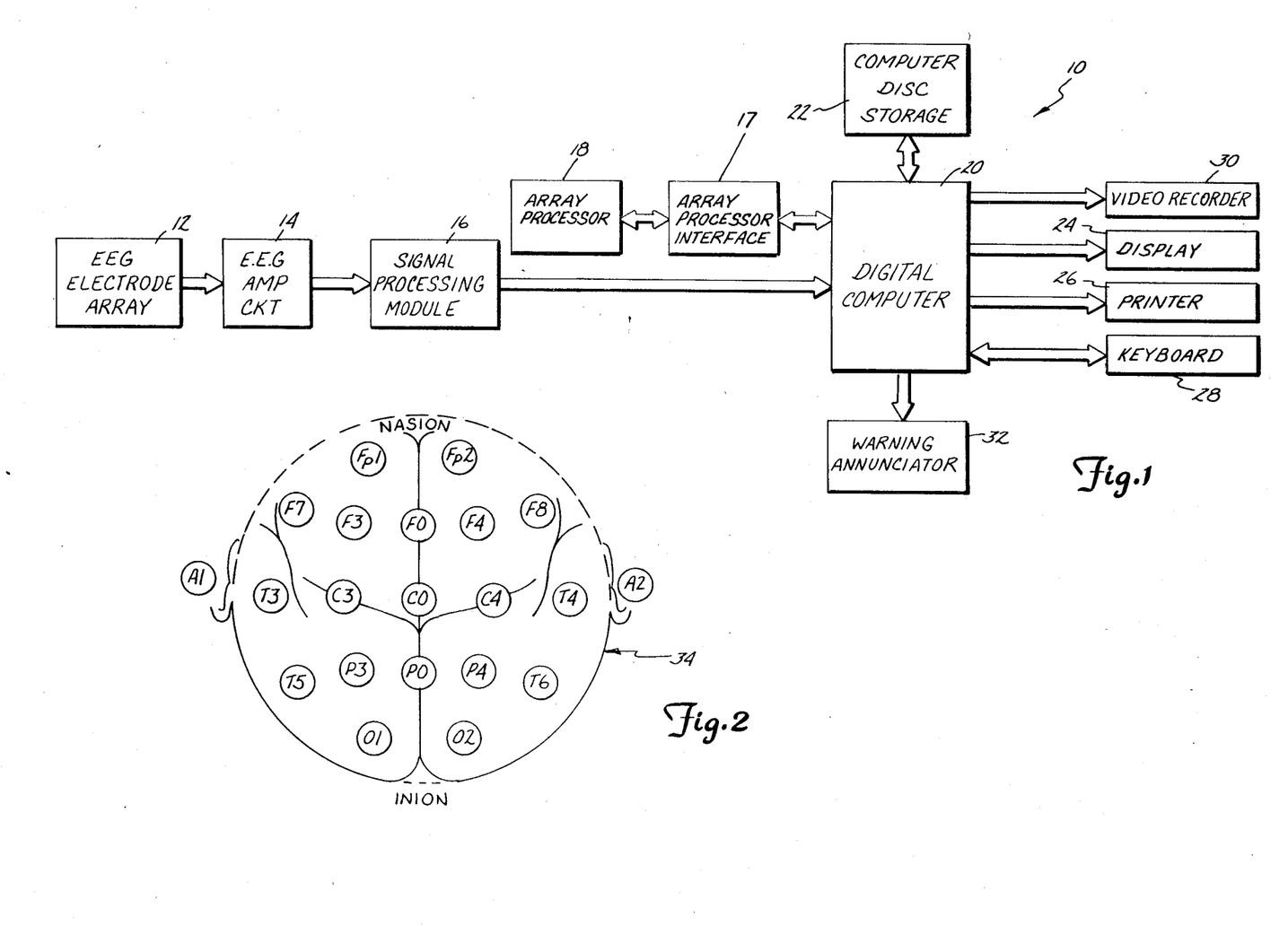
FIG. 1 is an electrical block diagram of a preferred embodiment of the real-time EEG spectral analyzer of the present invention.
FIG. 2 is a diagram illustrating typical electrode sites used in a sixteen-channel EEG electrode array.

FIG. 1 shows a preferred embodiment of the present invention in which real-time EEG spectral analyzer 10 includes EEG electrode array 12, EEG multichannel amplifier circuit 14, signal processing module 16, array processor interface 17, array processor 18, digital computer 20, computer disc storage 22, display 24, printer (or other hard copy device) 26, keyboard 28, video recorder 30, and warning annunciator 32. The purpose of the EEG spectral analyzer 10 is to record and analyze EEG signals and to provide an output on a real-time basis through display 24 or printer 26 which indicates the frequency response to EEG signals from various channels in each of the four frequency bands of interest (delta, theta, alpha and beta).

EEG electrode array 12 includes a plurality of EEG electrodes which are placed in contact with the scalp of a human subject. FIG. 2 is a diagram which illustrates nineteen typical sites of electrodes on a subject's head 34. When array 12 is used in a sixteen channel system, sixteen of the nineteen sites shown in FIG. 2 are used. In the diagram shown in FIG. 2, the electrode sites are identified by the commonly used designations Fp1, Fp2, F0, F3, F4, F7, F8, T3, T4, T5, T6, C0, C3, C4, P0, P3, P4, O1, and O2. Also shown are reference electrode sites (A1 and A2) for reference electrodes which are commonly attached to one (or both) of the subject's ears.

Each EEG channel represents one of the EEG electrode sites of array 12. EEG multichannel amplifier circuit 14 includes a differential amplifier for each channel, which amplifies the potential difference between a reference potential and the potential at the electrode site for that particular channel. The reference potential is derived from one or a combination of both of the reference electrode sites A1 or A2, or is based upon an average of the potentials from all of the sites, or is derived from an adjacent electrode site. The output of EEG multichannel amplifier circuit 14 is an analog EEG signal for each channel.

Signal processing module 16 receives the analog EEG signals from EEG multichannel amplifier circuit 14. Signal processing module 16 samples the analog EEG signal for each channel at a rate which is greater than twice the highest EEG signal frequency of interest. The sampled analog values for each channel are converted to digital values, and are stored by signal processing module 16. The sampling, digitizing and storing occurs over a continuing series of time intervals or "epochs". In a preferred embodiment, the lowest frequency of interest is one Hertz, and therefore each epoch has a duration of at least one second. The stored digital sample values for each channel represent the amplitude of the EEG signal as a function of time (i.e. a digitized waveform) during that epoch.

Figure 3:
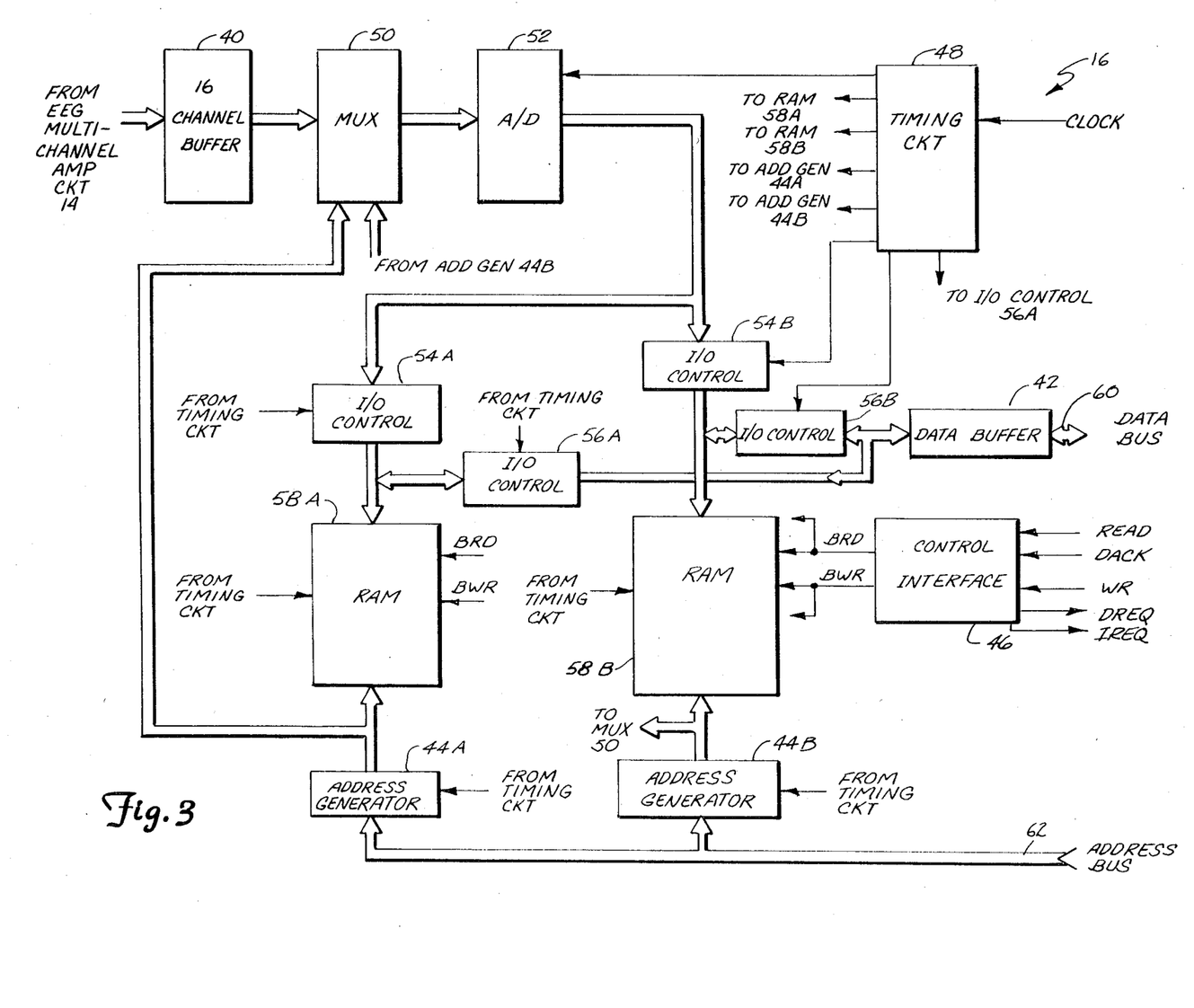
FIG. 3 is an electrical block diagram of a preferred embodiment of the signal processing module of the EEG spectral analyzer of FIG. 1.

FIG. 3 shows a block diagram of one preferred embodiment of signal processing module 16, which includes sixteen channel buffer/filter 40, data buffer 42, address generators 44A and 44B, control interface 46, timing circuit 48, multiplexer (MUX) 50, analog-to-digital converter (A/D) 52, input/output (I/O) controls 54A and 54B, I/O controls 56A and 56B, and random access memories (RAMs) 58A and 58B. Signal processing module 16 interfaces with EEG multichannel amplifier circuit 14 through sixteen channel buffer/filter 40. Signal processing module 16 interfaces with array processor interface 17 through data buffer 42, address generators 44A and 44B, control interface 46, and timing circuit 48. Data buffer 42 acts as a buffer between data bus 60 and signal processing module 16.

Address generator 44A receives addresses from address bus 62 of digital computer 20 during read operations and generates its own addresses during sampling operations, and provides those addresses to multiplexer 50 and RAM 58A. Similarly, address generator 44B receives addresses from address bus 62 during read operations and generates its own addresses during sampling operations, and provides those addresses to multiplexer 50 and RAM 58B.

Control interface 46 is connected to READ, DACK, WR, DREQ and IREQ lines of digital computer 20. Control interface 46 provides a read signal (BRD) and a write signal (BWR) to RAMs 58A and 58B based upon the control signals from digital computer 20.

Timing circuit 48 receives a synchronized clock signal from digital computer 20. The timing signals produced by timing circuit 48 based upon this synchronized clock signal are supplied to address generators 44A and 44B, A/D converter 52, I/O controls 54A, 54B, 56A and 56B, and RAMs 58A and 58B.

During a read operation, data is transferred by the digital computer 20 from the data buffer 42 through data bus 60 to the array processor 18 via array processor interface 17. In the embodiment shown in FIG. 1, signal processing module 16 samples, digitizes, stores and transfers data through digital computer 20 to array processor interface 17 and array processor 18. During alternating time intervals (which will be referred to as Intervals A and B), digitized waveforms are being written in one of the two RAMs 58A (or 58B) while digitized waveforms stored during the preceding time interval are being read from the other RAM 58B (or 58A) and transferred to array processor interface 17 and array processor 18 through digital computer 20. This arrangement permits continuous sampling of the EEG signals without delays for transferring the digitized waveforms to array processor 18. During Interval A, the analog EEG signals received from multichannel amplifier circuit 14 are buffered by sixteen channel buffer 40 and supplied to multiplexer 50. The analog EEG signal from one channel at a time is supplied by multiplexer 50 to A/D converter 52 to be sampled and digitized. The particular channel which is selected is based on an address from address generator 44A, which changes addresses at a rate determined by a timing signal from timing circuit 48. In a preferred embodiment of the present invention, a different channel is selected by multiplexer 50 each 245 microseconds. During one second, the analog EEG signal for each of the sixteen channels is sampled and digitized 256 times. It will be understood, however, that other sample rates can also be advantageously used in the present invention.

The digital sample values produced by A/D converter 52 during Interval A are supplied through I/O control 54A and are written into RAM 58A. Each sample value is stored in a different location of RAM 58A, which depends upon the address supplied by address generator 44A and the time at which the signal was sampled. When Interval A is completed, there are digital sample values stored in RAM 58A for each of the sixteen channels. These digital sample values represent the amplitude of the analog EEG signal for that particular channel as a function of time during Interval A.

During Interval A, timing circuit 48 also supplies timing signals to address generator 44B, I/O control 54B and RAM 58B which permits the stored data from RAM 58B to be read out of RAM 58B through I/O control 56B, and data buffer 42 onto data bus 60. This stored data which is read out and transferred to array processor 18 through digital computer 20 and array processor interface 17 represents the digitized waveforms stored in RAM 58B during the preceding Interval B.

During Interval B, the operations are reversed, with data being written into RAM 58B while data is being read out from RAM 58A. The digital sample values produced during Interval B by A/D converter 52 are supplied through I/O control 54B to RAM 58B. Each sample value is stored in a different location of RAM 58B, which depends upon the address supplied by address generator 44B and the time at which the signal was sampled. When Interval B is completed, there are digital sample values stored in RAM 58B for each of the sixteen channels. These digital sample values are digitized waveforms representing the amplitude of the analog EEG signals for each channel as a function of time during Interval B.

During Interval B, timing circuit 48 also supplies timing signals to address generator 44A, I/O control 54A, and RAM 58A which permits the stored data from RAM 58A to be read out of RAM 58A through I/O control 56A and data buffer 42 onto data bus 60. This stored data which is read out and transferred to array processor 18 represents the digitized waveforms stored in RAM 58A during the preceding Interval A.

The operation of signal processing module 16 continues with alternating Intervals A and B as long as spectral analyzer 10 is in operation. In a preferred embodiment of the present invention, Intervals A and B are each of one-second duration and together form epochs of two-second duration.

Array processor 18 converts the digitized waveforms received from signal processing module 16, through digital computer 20 from the time domain to the frequency domain. In a preferred embodiment of the present invention, array processor 18 is an Analogic AP494-06-01-B8 array processor card set, and array processor interface 17 is the interface circuitry necessary to make it compatible with digital computer 20 (which is preferably an IBM PC personal computer).

In this preferred embodiment of the present invention, array processor 18 transforms each digitized waveform from the time domain to the frequency domain by means of a Fast Fourier Transform (FFT). The use of array processor 18 to perform the Fast Fourier Transform function greatly reduces the processing time which would otherwise be required by digital computer 20 and thus enhances spectral analyzer 10 for operation on a real-time basis.

In preferred embodiments of the present invention, the data from each epoch is checked by array processor 18 prior to performing the Fast Fourier Transform. Those epochs which contain artifacts are rejected, and the digitized waveforms from those epochs are not transformed to the frequency domain or used subsequently by spectral analyzer 10.

One type of artifact which can result in erroneous information occurs when the analog EEG signals equal or exceed the voltage limit of A/D converter 52. In a preferred embodiment of the present invention, the voltage magnitude limit of A/D converter 52 is 5 volts. In this embodiment, any voltage magnitude greater than 5 volts will result in the same maximum/minimum output value from A/D converter 52. Since a saturated A/D converter output is the equivalent of a square wave and creates odd harmonics when a Fast Fourier Transform is performed, array processor 18 rejects any epoch containing amplitude magnitude values which are equal to or greater than 5 volts. This eliminates any epochs which would contain erroneous frequency values as a result of saturation of the A/D converter 52.

Another type of artifact which is detected by array processor 18 prior to the Fast Fourier Transform is the result of eye movement of the subject. Array processor 18 rejects any epoch which contains high amplitudes from the anterior sites (particularly FP1 and FP2). The presence of these high amplitudes (even if not equal to the saturation value of the A/D converter 52) at these particular sites indicates that eye movement has occurred which would result in erroneous information from that particular epoch.

The output of array processor 18 is a digitized frequency spectrum (amplitude as a function of frequency) for each channel during each epoch. This output is supplied by array processor 18 to digital computer 20 for further processing.

In a preferred embodiment of the present invention, digital computer 20 is an IBM personal computer which has its internal read/write random access memory (RAM) capacity increased to at least 96K bytes of data. Further read/write storage is provided by computer disc storage 22.

Digital computer 20 performs further artifact rejection on the data received from array processor 18. The frequency spectra are screened by digital computer 20 to identify any epoch which exhibits a significant high frequency component (greater than 30 Hertz) from a temporal site (such as T3, T4, F7, or F8). Such a high frequency component can be indicative of muscle artifacts, and any epoch containing such artifacts is rejected by digital computer 20.

In addition, digital computer 20 checks for artifacts caused by a loose lead to one of the electrodes of array 12. When a bipolar configuration is used (i.e. when each site uses an adjacent site as its reference), a slowing of the frequency response at two adjacent channels which share a common electrode may indicate the presence of a loose lead at that common electrode. Digital computer 20 checks amplitude values for the delta band and if two channels which share a common electrode both have delta amplitude values which are greater than a predetermined limit, digital computer 70 identifies the common electrode as having a loose lead. Digital computer 20 also checks the frequency spectra for unusually high amplitudes at 60 Hz. which also indicate loose lead artifacts. Digital computer 20 rejects the epochs which contain artifacts caused by loose leads, and also provides a diagnostic message to the operator through display 24 or printer 26, so that the loose lead can be corrected.

Digital computer 20 averages the frequency spectra from a number of artifact-free epochs over a predetermined update period. In one preferred embodiment of the present invention, in which the epochs are each of two-second duration, the update periods have a thirty second duration, so that a total of fifteen epochs are averaged in each update period if all epochs are artifact-free.

After the frequency spectra for each channel have been averaged for the update period, digital computer 20 calculates an amplitude value for each frequency band for each channel. This frequency band amplitude value is produced by summing the amplitude values of each frequency within the particular frequency band. The result is a data, a theta, an alpha and a beta amplitude value for each channel. Digital computer 20 then provides an output through display 24 and/or printer 26 based upon the frequency band amplitude values for the various channels. Each time another update period is completed, the information being displayed through display 24 is updated based upon the new frequency band amplitude values.

In one preferred embodiment of the present invention, during an initial update period digital computer 20 calculates and stores frequency band amplitude values as a base line. As each subsequent update period is completed, the frequency band amplitude values are compared at each channel to the base line values for that channel. If the updated amplitude values (or combinations of those values) vary from the base line amplitude values (or combinations) by greater than predetermined limits, digital computer 20 provides a warning indication through display 24 and/or printer 26, and also produces a warning signal through warning annunciator 32. This is particularly valuable when spectral analyzer 10 is being used for monitoring a patient during a surgical procedure such as a carotid endarterectomy. Spectral analyzer 10 provides a warning to the surgeon, so that corrective action such as the use of a shunt can be initiated immediately, before damage to the brain has occurred due to insufficient blood flow.

Similarly, providing a warning signal as a function of variance from base line values is valuable in order to monitor cerebral activity of a patient in an intensive care unit or recovery room.

Figure 4A:
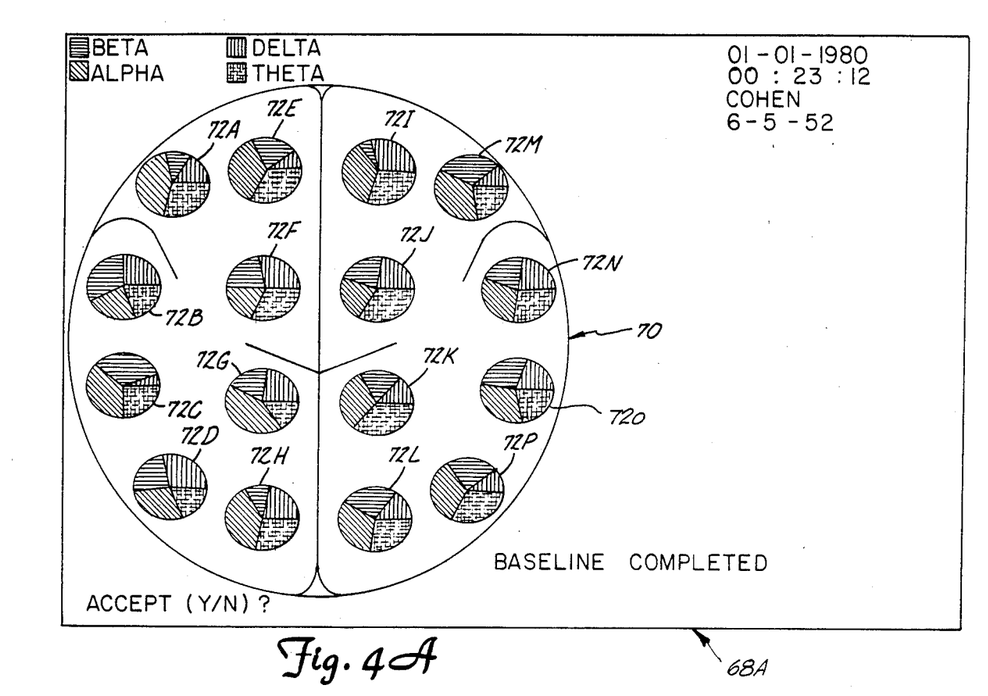
FIGS. 4A and 4B illustrate one form of displayed or printed output provided by the real-time spectral analyzer of the present invention.
Figure 4B:
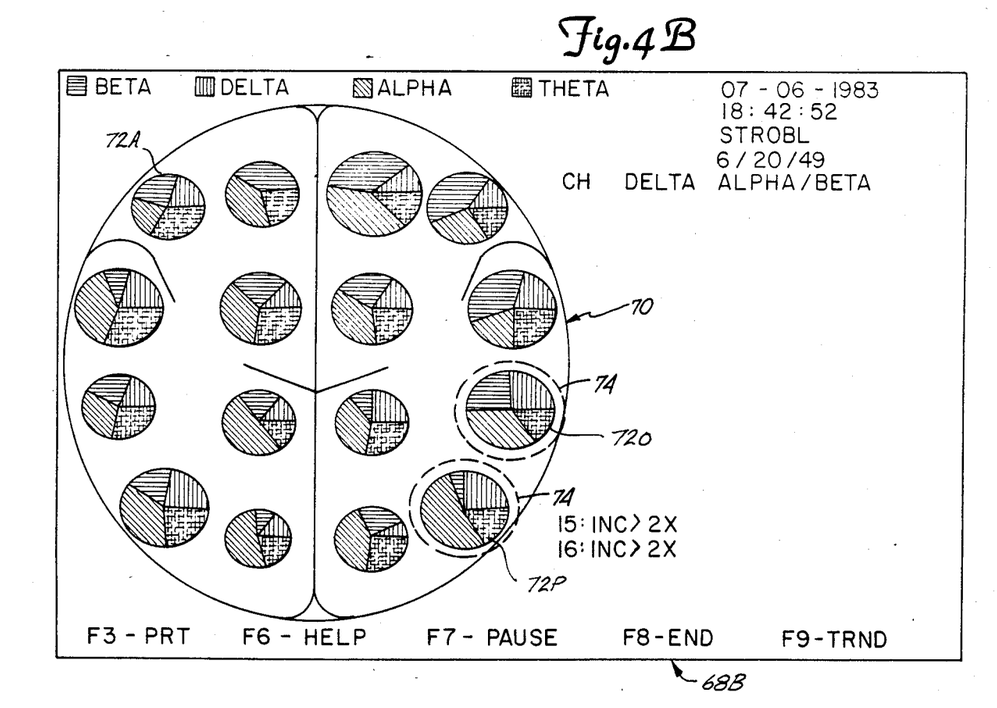

FIGS. 4A and 4B illustrate one preferred form of output which is provided by digital computer 20 through display 24 when a "circle display mode" is selected through keyboard 28. In FIGS. 4A and 4B, the output is in the form of a display screen 68A and 68B, respectively, which includes a graphic representation 70 of a patient's head, with sixteen circles 72A-72P representing the sixteen EEG channels. Each circle includes four pie-shaped segments which represent the comparative magnitude of the frequency band amplitude value. Each segment is a different color. In this example, beta is blue, delta is red, alpha is green and theta is yellow. Digital computer 20 calculates the size of each pie-shaped segment by dividing the amplitude value for that particular frequency band by the sum of the four amplitude values for that channel.

In FIG. 4A, the results of the base line measurement are illustrated. Head graphic 70 is shown in the left hand side of screen 68A. In the upper left hand corner, the color codes for the four frequency bands are shown. In the upper right hand corner, the date of the measurements, the time of day of the measurements (in hours, minutes, and seconds), the last name of the patient, and the year of birth of the patient are shown. In the lower right hand corner the message "BASE LINE COMPLETED" indicates the screen 68A is showing base line measurement data. In the lower left hand corner, a prompt message "ACCEPT (Y/N)?" is provided. The operator is given the option of accepting the base line measurements shown on screen 68 or of initiating another base line measurement by depressing the appropriate key of keyboard 28.

As shown in FIG. 4A, circles 72A-72P all have the same radius. This particular radius is the "base line radius". The total amplitude from the various channels normally are different, even during the base line period. All of the base line values, however, are normalized so that as long as base line conditions are repeated during subsequent update periods, the radius of the circle for any given channel will remain the same.

FIG. 4B shows screen 68B which is similar to screen 68A of FIG. 4A, except that it is subsequent to the base line period. As shown in FIG. 4B, circles 72A-72P have radii which in some cases differ from the base line radius. The radius of any given circle is determined by digital computer 20 based upon a comparison of the sum of the four amplitude values for that channel during the update period and the sum of the four amplitude values for that channel during the base line period. The radius is either increased, or decreased from the base line radius as a function of the variance of the sum of the amplitude values during the update period from sum for the base line period. As in FIG. 4A, each of the circles includes pie-shaped segments representing the relative proportions of the total amplitude at that channel contributed by delta, theta, alpha and beta frequency bands.

As described previously, digital computer 20 checks variance of the update amplitude values at each channel from the base line values for that same channel. When a particular amplitude value or a combination of amplitude values vary by greater than a predetermined limit, digital computer 20 provides an indication both visually through display 24 and by means of warning annunciator 32 of the excessive variance. In the particular example shown in FIG. 4B, digital computer 20 compares the updated delta amplitude values with the base line delta amplitude values and compares the sum of the update alpha and beta amplitude values with the sum of the base line alpha and beta amplitude values. This is indicated by the legend "CH DELTA ALPHA/BET" which appears to the right of head graphic 70. When the update delta amplitude is greater than the base line value by a predetermined limit (such as a factor of two), the channel is identified in the column below "CH" and a message is displayed in the column below "DELTA". Similarly, when the sum of the alpha and beta update values are less than the sum of the alpha and beta base line values by a predetermined limit (such as a factor of two) the channel is identified in the column under "CH" and and a message is displayed in the column below "ALPH/BET".

In the example shown in FIG. 4B each of circles 72N and 72P (representing "Channel 15" and "Channel 16") is outlined by a larger circle 74 (which preferably is in red or another bright color). This indicates that a greater than normal variance has occurred. The message displayed in the columns below "CH" and "DELTA" indicates that "Channel 15" and "Channel 16" each have update delta amplitude values which are greater than twice the base line beta amplitude value.

Along the lower edge of screen 68B shown in FIG. 4B, there is a message which indicates other functions which can be selected through keyboard 28. "F3-PRT" is a print function. When this function is selected, digital computer 20 causes printer 26 to print out the same information which is being displayed by display 24.

"F6-HELP" is a function in which digital computer 20 provides diagnostics information and prompts to the operator.

"F7-PAUSE" is a pause function which allows display 24 to hold the information currently being displayed. As update periods take place, that information is not used to update display 24 as long as the pause function is selected.

"F8-END" is an end function which terminates the operation of spectral analyzer 10.

Figure 5:
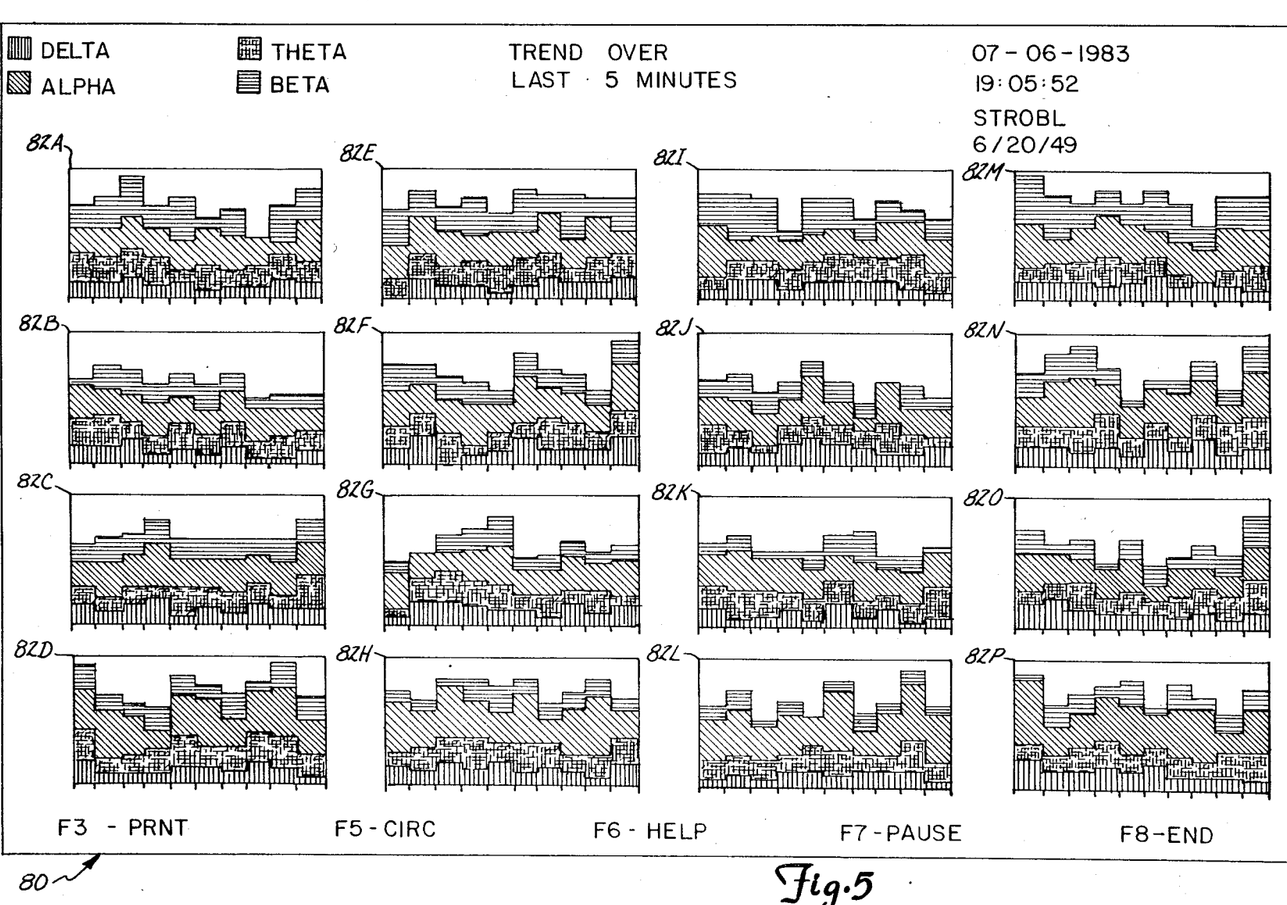
FIG. 5 shows another form of displayed or printed output provided by the real-time EEG spectral analyzer of the present invention.

"F9-TRND" is a trend function which provides graphical information of the frequency content at each of the sixteen channels over a period of time. The output provided when the trend function is selected is illustrated in FIG. 5, and comprises a screen 80 which includes sixteen individual bar graphs 82A-82P. Each of the graphs represents one of the sixteen EEG channels. In each graph, time is plotted along the horizontal axis and amplitude is plotted in the form of vertical bars. In the particular display 80 shown in FIG. 5, trends in frequency band amplitude values over a five-minute period is shown. The data is updated on a thirty second basis (although other user selected update time periods can be used as well), so that there are ten discrete update periods represented by ten side-by-side vertical bars shown in each graph 82A–82P.

When the trend mode is selected, screen 80 is updated every update period, with the oldest vertical bar of each graph 82A–82P being removed and all of the other bars being shifted to the left so that the newest update period is represented by the bar at the far right of each graph.

The trend function screen 80 shown in FIG. 5 provides an intuitive representation of both the total amplitude of the EEG signal at each channel over a period of time, and the contribution of each of the four frequency bands to that overall amplitude. Each of the four frequency bands is color coded and is presented in the same location in each of the graphs. In the particular embodiment shown in FIG. 5, the four bands are illustrated in ascending frequency order, with delta being on the bottom, followed by theta, alpha and beta.

In the upper left hand corner of screen 80, the color codes for the four frequency bands are indicated. As in FIGS. 4A and 4B, delta is red, theta is yellow, alpha is green and beta is blue.

In the top center of screen 80 the period over which the trend is illustrated is indicated. In this particular case, the graphs represent a trend over the previous five-minute period, although other periods can be selected.

In the upper right hand corner, the date of testing, the time of day (in hours, minutes and seconds), the last name of the patient, and the patient's birth date are all displayed in the upper right hand corner of screen 80.

Along the bottom of screen 80, codes indicating different functions which can be selected through keyboard 28 are indicated. Each of the function codes shown in FIG. 5 have already been discussed, except "F5-CIRC". This represents the circle display mode which is illustrated in FIGS. 4A and 4B.

Figure 6:
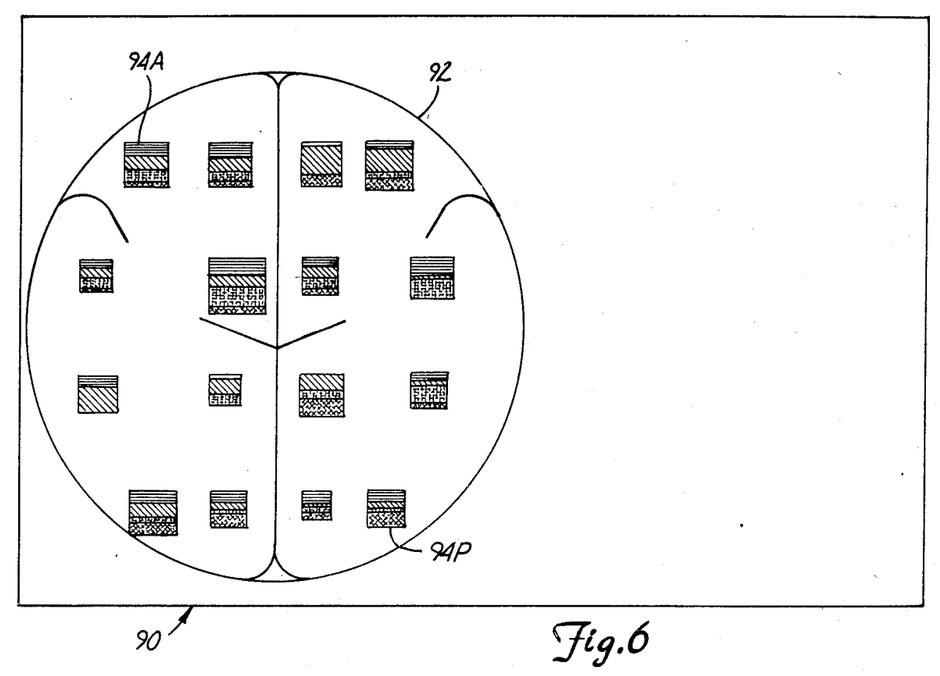
FIG. 6 illustrates another form of displayed or printed output which is generally similar to FIGS. 4A and 4B except that squares are used rather than circles.
Figure 7:
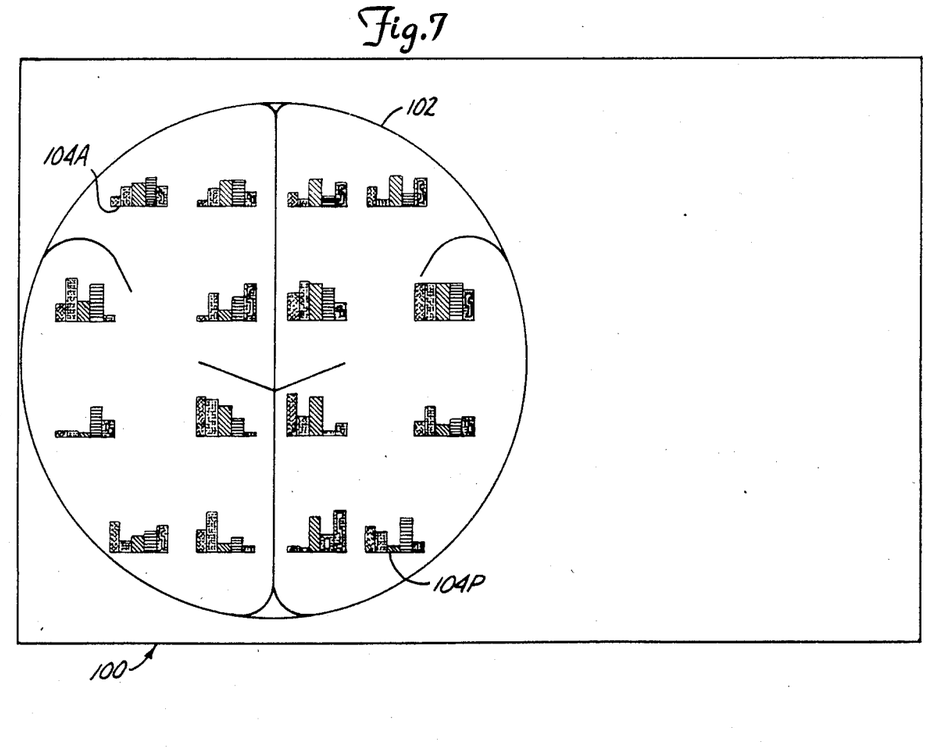
FIG. 7 illustrates still another form of displayed or printed output provided by the EEG spectral analyzer of the present invention.

Still other forms of output can be provided by spectral analyzer 10 are shown in FIGS. 6 and 7. In both of these examples, a head graphic with frequency band information for each of the channels is displayed.

FIG. 6 shows screen 90, which includes head graphic 92 and squares 94A–94P. Screen 90 is generally similar to screens 68A and 68B shown in FIGS. 4A and 4B, except that the frequency band information is displayed in the form of individual squares 94A–94P rather than circles 72A–72P. Each square 94A–94P has segments which represent the delta, theta, alpha, and beta frequency bands. These segments are in the form of horizontal bars rather than pie-shaped segments as shown in FIGS. 4A and 4B. The thickness of the horizontal bars is a function of the relative proportions of the total amplitude at that channel contributed by the particular frequency band. As in FIGS. 4A and 4B, beta is represented by the blue segment, delta by the red segment, alpha by the green segment, and theta by the yellow segment.

In FIG. 6, the area of each of the squares 94A–94B is a function of a comparison of the sum of the four amplitude values for that channel during the update period to the sum of the four amplitude values for that channel during the base line period. This is similar to the variation in area of circles 72A–72B shown in FIG. 4B as a function of variations in total amplitude.

Screen 100 shown in FIG. 7 includes head graphic 102 and bar graphs 104A–104P representing the sixteen channels being analyzed. Each bar graph 104A–104P includes five bars representing amplitude values for each of the four frequency bands and a total amplitude value. The red bar represents the delta frequency band, the yellow bar represents the theta frequency band, the green bar represents the alpha frequency band, and the blue bar represents the beta frequency band. The bar which is the furthest to the right of each group of five bars represents a sum of the amplitude values for the four frequency bands.

By comparing the height of the four frequency band bars for a particular channel, the relative proportion of each of the frequency bands at that channel can be determined. By comparing the height of the total amplitude bar at each of the various channels, the relative magnitude of the total EEG signals from each channel can be determined.

It will be appreciated that the particular forms of output illustrated in FIGS. 4A, 4B, 5, 6 and 7 represent only some of the possible forms of output which can be provided by spectral analyzer 10.

In the preferred embodiments of the present invention shown in FIG. 1, video recorder 30 is capable of recording the outputs provided by digital computer 20 to display 24. This permits the information which is displayed on a real-time basis by spectral analyzer 10 also to be recorded for subsequent review and study. This recording of data for later use is particularly advantageous when spectral analyzer 10 is used as a research tool, and also when spectral analyzer 10 is being used in a monitoring function.

In conclusion, the spectral analyzer of the present invention provides an intuitive display of EEG data which enhances the user's ability to understand and analyze that data. The updating of the display on a real-time basis makes the present invention applicable to a number of important applications which heretofore have not been possible or have been extremely inconvenient with prior art EEG equipment. These include monitoring within an operating room during surgical procedures, monitoring for on-line analysis for cerebral activity in intensive care, monitoring of patients or subjects during altered states of awareness or during psychological experimentation or assessment, monitoring in recovery rooms and intensive care units, and assisting in biofeedback training.

Although the present invention has been described with reference to preferred embodiments, workers skilled in the art will recognize that changes may be made in form and detail without departing from the spirit and scope of the invention.

What is claimed is:

1. A method of processing EEG signals from a plurality of channels to provide an output indicative of cerebral activity during a time period, the method comprising:

digitizing the EEG signals from the plurality of channels during a sequence of epochs of a known time duration to provide a digital waveform for each channel during each epoch;

transforming the digitized waveforms from a time domain to a frequency domain to produce a frequency spectrum for each epoch and channel;

averaging the frequency spectra for each channel over a plurality of epochs of the time period to produce an average frequency spectrum for each channel during the time period;

deriving, for each channel, frequency band amplitude values corresponding to a plurality of frequency bands based upon the average frequency spectrum for that channel; and providing an output indicative of cerebral activity in each of the frequency bands at each channel during the time period based upon the frequency band amplitude values.

2. The method of claim 1 wherein the average frequency spectrum comprises an amplitude value for each of a plurality of frequencies, and wherein deriving frequency band amplitude values comprises summing the amplitude value of all frequencies of the average frequency spectrum within each frequency band.

3. The method of claim 2 wherein the plurality of frequency bands includes a delta EEG frequency band, a theta EEG frequency band, an alpha EEG frequency band, and a beta EEG frequency band.

4. The method of claim 1 and further comprising:
rejecting any epoch, prior to transforming the digitized waveforms, which includes a digitized waveform having a characteristic indicative of an artifact.

5. The method of claim 4 wherein the characteristic is a presence of amplitude in the digitized waveform which is greater than a threshold value.

6. The method of claim 4 wherein the characteristic is indicative of an eye movement artifact.

7. The method of claim 6 wherein the characteristic is a presence of amplitudes greater than a threshold value from anterior channels.

8. The method of claim 1 and further comprising:
rejecting any epoch, after transforming the digitized waveforms, which includes a frequency spectrum having a characteristic indicative of an artifact.

9. The method of claim 8 wherein the characteristic is indicative of a muscle artifact.

10. The method of claim 8 wherein the characteristic is a presence of high frequency components in the frequency spectra corresponding to temporal channels.

11. The method of claim 8 wherein the characteristics are indicative of a loose lead artifact.

12. The method of claim 1 wherein providing an output comprises:
providing a visual output in graphical form which includes a graph for each channel, each graph including a segment representative of each of the frequency bands, each segment having a relative size which is a function of the frequency band amplitude value for the frequency band corresponding to that segment.

13. The method of claim 12 wherein each segment has a size which is a function of a ratio of the frequency band amplitude value for that segment and a sum of the frequency band amplitude values for the channel.

14. The method of claim 13 wherein each graph has an area which is a function of the sum of the frequency band amplitude values for the channel.

15. The method of claim 14 and further comprising:
storing the frequency band amplitude value from a selected period as base line frequency band amplitude values; and
wherein the area of each graph is based upon a comparison of a sum of the frequency band amplitude values for the corresponding channel during the time period to a sum of the base line frequency band amplitude values for that channel.

16. The method of claim 12 wherein providing an output further comprises:
providing a graphical representation of a human subject's head; and
positioning each of the graphs with respect to the graphical representation of the human subject's head to indicate the respective locations of the channels corresponding to the graphs.

17. The method of claim 1 and further comprising:
storing the frequency band amplitude values from a selected time period as base line frequency band amplitude values;
comparing the frequency band amplitude values from each time period with the stored base line frequency band amplitude values; and
providing a warning indication when a variance between the frequency band amplitude values of the time period and the stored base line frequency band amplitude values exceeds a variance threshold.

18. The method of claim 17 wherein providing a warning indication includes:
providing an audible signal when the variance exceeds the variance threshold.

19. The method of claim 17 wherein providing the warning indication includes:
providing a visual indication of the channel which provided the frequency band amplitude values for which the variance exceeded the variance threshold.

20. The method of claim 1 wherein providing an output comprises:
providing a graph for each channel showing a series of time periods with a segment of variable size corresponding to each of the frequency band amplitude values for that channel during each time period of the series.

21. The method of claim 20 wherein the graph for each channel comprises a series of bar graphs arranged in side-by-side relationship and representing the series of time periods, and wherein the segment for each frequency band has a length which is a function of the frequency band amplitude value during a corresponding time period.

22. A method of processing an analog EEG signal to provide an output indicative of cerebral activity and providing an output which is periodically updated, the method comprising:
digitizing the analog EEG signal during a sequence of epochs of a known time duration to provide a digitized waveform for each epoch;
transforming the digitized waveform for each epoch from a time domain to a frequency domain to produce a frequency spectrum for that epoch;
averaging frequency spectra from a plurality of epochs corresponding to an update period to produce an average frequency spectrum;
deriving a delta EEG frequency band amplitude value, a theta EEG frequency band amplitude value, an alpha EEG frequency band amplitude value, and a beta EEG frequency band amplitude value based upon the average frequency spectrum; and
periodically updating a output to provide an indication of the cerebral activity in the delta, theta, alpha and beta EEG frequency bands during a completed update period based upon the frequency band amplitude values for that update period.

23. The method of claim 22 wherein the average frequency spectrum comprises an amplitude value for each of a plurality of frequencies, and wherein deriving frequency band amplitude values comprises summing the amplitude values of all frequencies of the average frequency spectrum within each frequency band.

24. The method of claim 22 and further comprising:
rejecting any epoch, prior to transforming the digitized waveform, for which the digitized waveform has a characteristic indicative of an artifact.

25. The method of claim 22 and further comprising:
rejecting any epoch, after transforming the digitized waveform, for which the frequency spectrum has a characteristic indicative of an artifact.

26. The method of claim 22 wherein periodically updating an output comprises:
providing a visual output in graphical form which includes a segment representative of each of the frequency bands, each segment having a relative size which is a function of the frequency band amplitude value for the frequency band corresponding to that segment.

27. The method of claim 26 wherein each segment has a size which is a function of a ratio of the frequency band amplitude value for that segment and a sum of the frequency band amplitude values.

28. The method of claim 27 wherein the graphical form has an area which is a function of the sum of the frequency band amplitude values.

29. The method of claim 28 and further comprising:
storing the frequency band amplitude values from a selected update period as base line frequency and amplitude values; and
wherein the area of the graphical form is based upon a comparison of a sum of the frequency band amplitude values during the update period to a sum of the base line frequency band amplitude values.

30. The method of claim 22 and further comprising:
storing the frequency band amplitude values from a selected update period as base line frequency band amplitude values;
comparing the frequency band amplitude values from each update period with the stored base line frequency band amplitude values; and
providing a warning indication when a threshold variance occurs between the frequency band amplitude values of the update period and the stored base line frequency band amplitude values.

31. The method of claim 22 wherein periodically updating an output comprises:
providing a graph showing a series of update periods with a segment of variable size corresponding to each of the frequency band amplitude values during each update period of the series.

32. A system for processing EEG signals from a plurality of channels to provide an output indicative of cerebral activity, the system comprising:
means for digitizing EEG signals from the plurality of channels during a sequence of epochs of a known time duration to provide a digital waveform of amplitude as a function of time for each channel during each epoch;
means for transforming the digitized waveforms for each epoch and channel from a time domain to a frequency domain to produce a frequency spectrum of amplitude as a function of frequency for each epoch and channel;
means for averaging the frequency spectra for each channel from a plurality of epochs of an update period to produce an average frequency spectrum for each channel during the update period;
means for deriving a frequency band amplitude value for each of a plurality of frequency bands based upon the average frequency spectrum for each channel;
means for displaying a visual representation of cerebral activity in each of the frequency bands at each channel as a function of display control signals; and
means for periodically updating the display control signals as each update period is completed based upon the frequency band amplitude values for that update period.

33. The system of claim 32 wherein the means for deriving a frequency band amplitude value sums the amplitude values of all frequencies of the average frequency spectrum within each frequency band to produce the frequency band amplitude value.

34. The system of claim 32 wherein the plurality of frequency bands includes a delta EEG frequency band, a theta EEG frequency band, an alpha EEG frequency band, and a beta EEG frequency band.

35. The system of claim 32 and further comprising:
means for rejecting any epoch which includes a digitized waveform having a characteristic indicative of an artifact.

36. The system of claim 32 and further comprising:
means for rejecting any epoch which includes a frequency spectrum having a characteristic indicative of an artifact.

37. The system of claim 32 wherein the visual representation comprises a graph for each channel, each graph including a segment representative of each of the frequency bands, each segment having a relative size which is a function of the frequency band amplitude value for the frequency band corresponding to that segment.

38. The system of claim 37 wherein each each segment has a a size which is a function of a ratio of the frequency band amplitude value for that segment and a sum of the frequency band amplitude values for the channel.

39. The system of claim 38 wherein the means for periodically updating determines an area of each graph as function of the sum of the frequency band amplitude values for the channel corresponding to that graph.

40. The system of claim 39 and further comprising:
means for storing the frequency band amplitude values from a selected update period as base line frequency band amplitude values; and
wherein the means for periodically updating determines the area of each graph based upon a comparison of a sum of the frequency band amplitude value for the corresponding channel during the update period to a sum of the base line frequency band amplitude value for that channel.

41. The system of claim 37 wherein the visual representation further comprises:
a graphical representation of a human subject's head, the graphs being positioned with respect to the graphical representation of the human subject's head to indicate the respective locations of the channels corresponding to the graphs.

42. The system of claim 32 and further comprising:

means for storing the frequency band amplitude values from a selected update period as base line frequency band amplitude values;

means for comparing the frequency band amplitude values from each update period with the stored base line frequency band amplitude values; and means for providing a warning indication when a threshold variance occurs between the frequency band amplitude values of the update period and the stored base line frequency band amplitude values.

43. The system of claim 32 wherein the visual representation comprises a graph for each channel showing a series of update periods with a segment of variable size corresponding to each of the frequency band amplitude values for that channel during each update period of the series.

* * * * *